United States Patent [19]

Scherer, Jr. et al.

[11] Patent Number: 4,686,024

[45] Date of Patent: Aug. 11, 1987

[54] NOVEL PERFLUORO CHEMICALS AND POLYFLUORINATED COMPOUNDS AND PROCESS FOR PRODUCTION OF THE SAME

[75] Inventors: Kirby V. Scherer, Jr., Santa Monica, Calif.; Taizo Ono, Kyoto, Japan; Kouichi Yamanouchi; Kazumasa Yokoyama, both of Osaka, Japan

[73] Assignee: The Green Cross Corporation, Osaka, Japan

[21] Appl. No.: 697,552

[22] Filed: Feb. 1, 1985

[51] Int. Cl.$^4$ ............................................. C07C 41/00
[52] U.S. Cl. ........................... 204/157.95; 204/157.96; 204/157.97; 204/158.1; 204/158.11; 260/694; 568/677; 568/683; 568/685; 568/634

[58] Field of Search ........... 204/158 HA, 163, 157.94, 204/157.96, 157.97, 158.1, 158.11, 157.95; 568/677, 683, 685, 610, 639, 614, 645, 615, 647, 634, 637; 570/127; 260/694

[56] References Cited

U.S. PATENT DOCUMENTS 3,609,196  9/1971  Terrell ........................ 204/158 HA
3,897,502  7/1975  Russell et al. ...................... 568/677

*Primary Examiner*—John F. Niebling
*Assistant Examiner*—Ben Hsing
*Attorney, Agent, or Firm*—Sughrue, Mion, Zinn, Macpeak & Seas

[57] ABSTRACT

The present invention relates to novel perfluoro chemicals (PFC), particularly perfluorocyclic ethers and polyfluorinated compounds containing a few chlorine atoms and to a method for the preparation thereof.

3 Claims, No Drawings

NOVEL PERFLUORO CHEMICALS AND POLYFLUORINATED COMPOUNDS AND PROCESS FOR PRODUCTION OF THE SAME

FIELD OF THE INVENTION

The present invention relates to novel perfluoro chemicals (PFC), particularly perfluorocyclic ethers and polyfluorinated compounds containing a few chlorine atoms and to a method for the preparation thereof.

BACKGROUND OF THE INVENTION

Clark and Gollan's discovery triggered the investigation on the possible use of PFC as oxygen-carrying fluids and Slovitor and Geyer's breakthrough using PFC in an emulsified form has made it realistic. One of the most important factors relating to the realization of such oxygen-carrying fluids is the synthesis of PFC which are non-toxic, have high oxygen and carbon dioxide solubilities, are stable as an emulsion for 2 years even at room temperature; and are easily removable from the body in an unchanged form after accomplishing its role with the formation of the natural blood.

Various PFC are disclosed in patents, wherein they are described as being suitable as an oxygen and carbon dioxide carrier. Almost all of the PFC patented are prepared by the electrochemical fluorination method or the cobalt trifluoride method. The cobalt trifluoride method, which is excellent in preparing perfluorohydrocarbon, is too vigorous to fluorinate ethers. That is, degradation products are caused by the cleavage of oxygen and carbon bonds. The electrochemical fluorination method, which is excellent in preparing perfluoro amine, has limited utility in preparing perfluoro cyclic ethers. Therefore, in general, perfluorocyclic ethers, which are believed to be suitable as an oxygen and carbon dioxide carrier, remain to be synthesized. The exception are the ones synthesized by the electrochemical fluorination method, such as those set forth below:

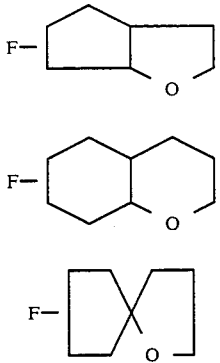

described by Abe et al (e.g., T. Abe, E. Hayashi, H. Baba and S. Nagase: *J. Fluorine Chem.* 25:419 (1984), and Japanese Patent Application (OPI) Nos. 119449/79, 119471/79, 128566/79 and 44071/80.

In the present invention, the substrates followed by the prefix "perfluoro" mean substrates having all of the hydrogens replaced by fluorine atoms but containing no halogens such as chlorine, bromine and iodine, and they may be cyclic or straight-chain compounds. Furthermore, polyfluorinated compounds with a few chlorine atoms denote substrates wherein the hydrogens are mostly replaced by fluorines, but the rest of the hydrogens, usually one or two hydrogens, are replaced by chlorine atoms.

SUMMARY OF THE INVENTION

It has now been found, in accordance with the present invention, that the combined use of F-hexane (FC-72) and 1,1,2-trichloro-1,2,2-trifluoroethane (F113) as a reaction medium or solvent for the substrate in liquid-phase photofluorination broadens the substrate spectrum applicable to this method from partially fluorinated substrates to unfluorinated substrates. Therefore, perfluorocyclic ethers, which have been difficult to prepare by the conventional method such as the cobalt fluoride method as described in *Industrial and Engineering Chemistry*, 39:292 (1947) and *J. Appl. Chem.*, 2:127 (1952), or electrochemical fluorination method, are now available as a result of the present invention.

The perfluorocyclic ethers and other compounds synthesized herein are perfluoro derivatives of $C_{10}$ ethers having mono- or bi-cyclic structures. Moreover, if only F113 is used, concomitant chlorination along with the fluorination occur and in the case of the fluorination of adamantane, mono- or di-chloro derivatives of perfluoroadamantane can be obtained. Therefore, by regulating the mixing ratio of F113 and F-hexane, both chlorofluorination and fluorination can be controllably carried out, as exemplified by the fluorination of decalin and adamantane described below.

It has been found that if one bromine atom is introduced into a PFC, the critical solution temperature (C.S.T.) of such a bromine-replaced PFC is drastically lowered compared to the starting PFC. This effect on the lipophilicity of PFC is desirable from the viewpoint of the excretion rate, but the bromine can act as a hook to be attacked by some chemical reagents (e.g., conc. $H_2SO_4$).

Although the effect of chlorine might be less than the effect of bromine, it is easy to estimate that chlorine has the same kind of effect on the C.S.T. of PFC cf. c-$C_8Cl_3F_{13}O$ is miscible with benzene, while c-$C_8F_{16}O$ is only slightly soluble. (George Van Dyke Tiers, *J. Am. Chem. Soc.*, 77:4837 (1955)).

Contrary to the situation where a bromine atom is present, the chlorine atom embedded in the PFC framework is shielded by fluorine atoms against chemical attack. Further, replacement by a fluorine atom by the cobalt trifluoride method is difficult. (R. E. Banks, R. N. Haszeldine and J. B. Valton, *J. Amer. Chem. Soc.*, 5581 (1963) and R. J. Heitzman et al, *J. S. C.*, 281 (1963).) This inertness of chlorine was investigated through the Manhattan Project and it is concluded in its voluminous report that monochloropentadecafluoroheptane is inert enough for use in the gas-diffusion method of separating uranium isotopes as well as perfluoroheptane. (Slesser and Schram, "Preparation, Properties and Technology of Fluorine and Organic Fluorocompounds", Part IIIA, Chapter 16–23.)

It is clear from the above discussion, that chlorine-containing perfluoro chemicals have desirable properties as oxygen-carrying fluids.

DETAILED DESCRIPTION OF THE INVENTION

The PFC of the invention have high oxygen and carbon dioxide solubility and no toxicity. The emulsion prepared thereof possess high stability and low body tissue retention. The fluorine containing compounds of the invention are the perfluoro and polyfluorinated derivatives of $C_{10}$ mono-cyclic or bi-cyclic-structure-bearing ethers other fluorine containing compounds.

Examples thereof include the following compounds.

(1) F-3,4-dimethyl-bicyclo(4,4,0)-2,5-dioxadecane

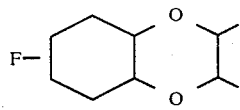

(2) F-1,3,3-trimethyl-bicyclo(2,2,2)-2-oxaoctane

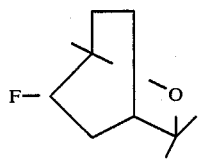

(3) F-3-ethyl-bicyclo(3,4,0)-2-oxanonane

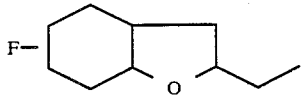

(4) F-cyclohexylmethyl isopropyl ether

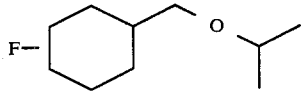

(5) F-1-(2-chlorocyclopentyl)cyclopentyl ether

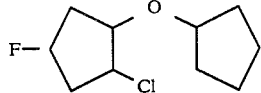

(6) F-1-(2-chlorocyclopentyl)n-pentyl ether

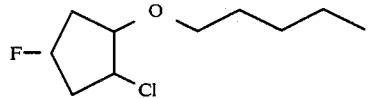

(7) F-2-ethyl-3,6,7-trimethyl-1,5-dioxepane

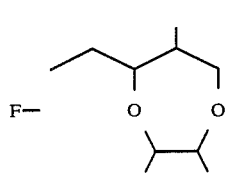

(8) F-2-ethyl-2-isopropyl-4,5-dimethyl-1,3-dioxole,

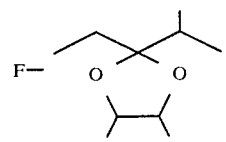

and also of mono- and di- and tri-chloro-polyfluoro adamantanes and F-adamantane

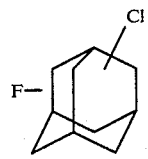

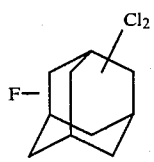

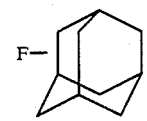

In the formulae shown herein "F-" means that the compound is perfluorinated unless otherwise indicated.

This invention also includes the partially fluorinated starting materials to be fluorinated by the present process.

Examples of such partially fluorinated starting materials thereof include the following compounds:

(9) 2-(F-ethyl)-2-(2-H-hexafluoroisopropyl)-4,5-dimethyl-1,3-dioxole

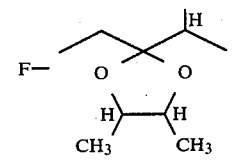

(10) 2,4-difluoro-4-(F-ethyl)-3-(F-methyl)-6,7-di-methyl-1,5-dioxepan-2-ene

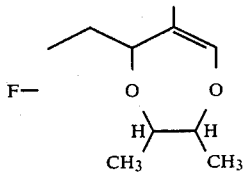

(11) 4,4-difluoro-2-(F-ethyl)-3-(F-methyl)-6,7-di-methyl-1,5-dioxepan-2-ene

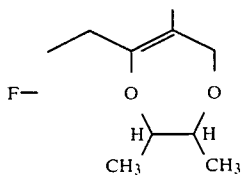

(12) 2,4,4-trifluoro-2-(F-ethyl)-3-(F-methyl)-6,7-dimethyl-1,5-dioxepane

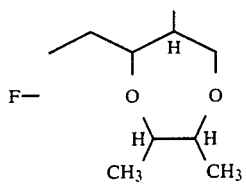

(13) 2-chlorohexafluorocyclopentenyl cyclopentyl ether

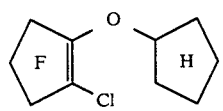

(14) 2-chlorohexafluorocyclopentenyl 2,2,3,3,4,4,5,5-octafluoro-n-pentenyl ether

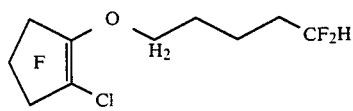

(15) 5,6,7,8-tetrafluoro-2,3-dimethyl-1,4-benzodioxin

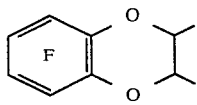

All of the unmarked bonds are to fluorine and H inside a ring denotes that the bonds of the ring moiety with H are saturated with hydrogen atoms.

The perfluorination can be conducted by the liquid-phase photofluorination method of Scherer and Yamanouchi (U.S. patent application Ser. No. 582,448, filed Feb. 22, 1984).

More particularly, the PFC of the present invention is prepared from a partially fluorinated or non-fluorinated compound by a liquid phase fluorination method wherein:

(a) the fluorination is carried out at −75 to +100° C. in an inert liquid medium;

(b) the inert liquid medium is F-hexane (FC-72) and/or 1,1,2-trichloro-1,2,2-trifluoroethane (F-113);

(c) undiluted or diluted fluorine ($F_2$) is used;

(d) the $F_2$ is maintained in stoichiometric excess at all times, so that the intermediate carbon radicals react with $F_2$ rather than each other;

(e) the compound to be fluorinated is metered in slowly with vigorous stirring, so that it is rapidly diluted by the solvent and its concentration is kept low compared to $F_2$, and so that efficient heat dispersal occurs;

(f) UV illumination is used to initiate the fluorination reaction if spontaneous initiation is not sufficiently rapid.

In the method of the present invention, F-hexane and/or F113 is used as an inert liquid medium.

The key points in operation of the present process are as follows:

(a) The perfluorination is carried out at −75° C. to +100° C., preferably −30° to +25° C., in an inert liquid medium; preferably a perfluoro chemical which may be the reaction product itself;

(b) Either F-hexane or F113 or a mixture thereof can be used as an inert liquid medium;

(c) Molecular fluorine itself, that is, undiluted or diluted $F_2$ is used as perfluorinating agent;

(d) The $F_2$ is maintained in stoichiometric excess at all times during the reaction, so that the intermediate carbon radicals react with $F_2$ rather than each other;

(e) The compound to be perfluorinated is metered and charged in slowly with vigorous stirring, so that it is rapidly diluted by the solvent and its concentration is kept low compared to $F_2$, and so that efficient heat dispersal occurs; and preferably, (f) UV irradiation, preferably of wavelength 240 to 330 nm is used to initiate the fluorination reaction if spontaneous initiation is not sufficiently rapid, and further preferably;

(g) The reaction is preferably carried out by employing UV illumination, to smoothly give the corresponding perfluorinated compounds in high yield.

The substrate or starting material for preparing the PFC of the present invention which can be used in the present process include any partially fluorinated or non-fluorinated compounds as long as they are soluble in F-hexane or F113.

Examples of the partially fluorinated compounds include compounds of formulae (10) to (15) described hereinabove, those compounds described in U.S. Ser. No. 582,448, filed Feb. 22, 1984, and the like.

These partially fluorinated compounds can be prepared according to the conventional methods described in J. C. Tatflow et al, *J. Chem. Soc.*, 763 (1964); N. Ishikawa et al, *Nihon Kagakukaishi*, p. 563–7 (1973); N. Ishikawa et al, *J. Fluorine Chem.*, 18:447–57 (1981); M. Murata et al, *J. Fluorine Chem.*, 16:75–88 (1980); and U.S. Ser. No. 582,448.

Examples of the non-fluorinated compounds include ethers having a cyclic structure (such as cyclopentenyl pentyl ether), cyclic ethers (such as chromene derivatives), tertiary amines (such as tricpropylamine), cyclic amines (such as N-methyldecahydroisoquinoline), condensed polycyclic hydrocarbons (such as naphthalene, decalin, adamantane), etc.

If the substrate to be fluorinated is sparingly soluble in F-hexane, F113 is used as co-medium and/or as the solvent for the substrate. Elemental fluorine gas is preferably used in this process, but it is not essential. Therefore, fluorine gas diluted with inert gas such as nitrogen, helium and argon is also usable in this process.

Preparation of the Starting Substrate

The preparation of the starting substrate is carried out based on typical fluorine chemistry such as the nucleophilic substitution of perfluoroolefins and hexafluorobenzene with various nucleophiles.

The present invention is further illustrated by the following examples which should not be construed as limiting the present invention thereto.

EXAMPLE 1

2,3-Butanediol (2.7 g, 0.03 mol) was added to a mixture of perfluoro-2-methyl-2-pentene (D-II) (10.8 g, 0.036 mol) and triethylamine (6.06 g, 0.06 mol) in 60 ml of acetonitrile. The mixture was stirred with a magnetic stirrer for 1 hour at room temperature. The reaction mixture was poured into water (200 ml) and an organic layer was separated. The aqueous layer was extracted with 4 portions of 50 ml of F113. The organic layer and the extracts were combined and dried over sodium sulfate overnight. F113 was distilled out and that which remained was distilled under reduced pressure using a semi-micro distilling apparatus with a 6-inch jacketed column to give 6 fractions whose compositions are summarized in the following table.

The substance (4.6 g) collected in a trap cooled by liquid nitrogen was almost pure (I) (41% yield).

| Fraction | Boiling Range (°C.) | Amount (g) | (I) (%) | (II) (%) | (III) (%) |
|---|---|---|---|---|---|
| Trap | | 4.60 | 93 | 7 | — |
| F-1 | 28–35/1.7 mmHg | 0.39 | 63 | 37 | — |
| F-2 | 35–36/1.7 mmHg | 0.35 | 43 | 57 | — |
| F-3 | 43–46 | 0.99 | 22 | 73 | 5 |
| F-4 | 50–52 | 0.77 | 9 | 83 | 8 |
| F-5 | 52–57 | 0.78 | — | 86 | 14 |
| F-6 | 57–60 | 0.38 | — | 79 | 21 |
| Residue | | 1.45 | — | 25 | 75 |

The $^{19}$F-NMR data for each chemical structure (CFCl$_3$ reference) depicted below is also provided.

(I)

(−120.7, −121.5) CF$_3$
1:5
(−76.7, −76.4) CF$_3$—CF$_2$—C—CH—CF$_3$ } −57.3, −58.3
O     O
\\CH——CH/
CH$_3$   CH$_3$ (II)

CF$_3$ −51.5
−112.5
−77.5 CF$_3$—CF$_2$—CF−48.8—C=CF (−40.9, −44)
O     O     1:2
\\CH——CH/
CH$_3$   CH$_3$ (III)

CF$_3$ −46.7
−123.1
−75.5 CF$_3$—CF$_2$—C=CF −100.1
O     O
\\CH——CH/
CH$_3$   CH$_3$

EXAMPLE 2

Triethylamine (6.06 g, 0.06 mol) was added to a solution of D-II (10.8 g, 0.036 mol) in 30 ml of F113 to give a suspension of a complex thereof. Into this suspension was added 2,3-butanediol (2.7 g, 0.03 mol) dispersed in 90 ml of F113 with vigorous stirring.

The insoluble material which arose after stirring for 18 hours at room temperature was filtered off, and F113 was distilled out. The resulting material was distilled in the same manner as in Example 1 to give 3 fractions whose compositions are summarized in the following Table.

| Fraction | Boiling Range (°C.) | Amount (g) | (I) (%) | (II) (%) | (III) (%) | (IV) (%) |
|---|---|---|---|---|---|---|
| Trap | | 4.15 | 6.7 | 4 | 1 | — |
| F-1 | 35–45/0.6 mmHg | 5.72 | 1.1 | 4 | 1 | — |
| F-2 | 45 | 0.4 | — | 1.7 | 1 | — |
| F-3 | 55–65 | 4.88 | — | — | 1 | 6.4 |

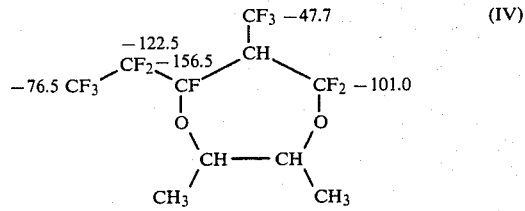

(IV)

Chemical shifts are minus toward upper field from CFCl$_3$.

EXAMPLE 3

Cyclopentanol (23 g, 0.27 mol) and sodium metal (5.6 g, 0.24 mol) were refluxed with 25 ml dry tetrahydrofuran (THF) overnight. The reaction mixture was diluted with 200 ml of dry ether and then added to 1,2-dichlorohexafluorocyclopentene (49 g, 0.2 mol) in 100 ml of dry ether at room temperature with stirring over 20 minutes. After the completion of the addition, the reaction mixture was heated to reflux for 2 hours. The reaction mixture was poured into ice water (150 ml) and the organic layer was separated. Then the aqueous layer was extracted with 4 portions of 100 ml of ether. Next, the organic layer and the ether extracts were combined and dried over CaCl$_2$ overnight. Thereafter, the solvent was distilled out at atmospheric pressure. That which remained was distilled under reduced pressure to give the desired 2-chlorohexafluorocyclopentenyl cyclopentyl ether in 79% yield based on the 1,2-dichlorohexafluorocyclopentene used.

The $^{19}$F-NMR measured shows three signals with relative intensities 1:1:1 at −106.1, −111.1 and −125.5 ppm from the CFCl$_3$ reference. Molecular ion (m/z 294, 296),

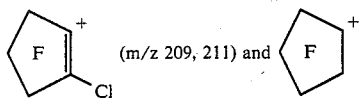

(m/z 69) were found in the mass spectrum.

EXAMPLE 4

2,2,3,3,4,4,5,5-Octafluoro-n-pentanol (11.6 g, 0.05 mol) and sodium metal (1.4 g, 0.05 mol) were added to 100 ml of dry ether and stirred at room temperature overnight. The solution obtained was added into a solution of 1,2-dichlorohexafluorocyclopentene (12.3 g, 0.05 mol) in 100 ml of dry ether. The reaction mixture was poured into 150 ml of ice water and an organic layer was separated. The aqueous layer was then extracted with 3 portions of 100 ml ether. Next, the extracts were combined with the separated organic layer and dried over sodium sulfate overnight. The desired 2-chlorohexafluorocyclopentyl 2,2,3,3,4,4,5,5-octafluoro-n-pentyl ether (38°–42° C./0.3 mmHg) was obtained in 50% yield based on 1,2-dichlorohexafluorocyclopentene used by vacuum distillation.

The $^{19}$F-NMR (neat $\phi^*$): −108.3 (2F), −110.5 (2F), and −126.1 (2F) are to F$_3$ on the ring and −117.2 (2F), −121.3 (2F), −126.1 (2F), −134.5 (2F) are to the one alkyl chain. MS: M$^+$ (m/z 440, 442), M-F$^+$ (m/z 421, 423),

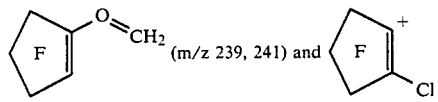

(m/z 209, 211) were observed in relative intensities of (48.9, 16.6) (18.0, 5.7), (85.9, 28.1) and 100, 33.8), respectively.

EXAMPLE 5

Hexafluorobenzene (13.9 g, 0.11 mol) and 2,3-butanediol (67.7 g, 0.72 mol) were refluxed in the presence of 1.15 mol of NaOH. After work up of the 3-hydroxy-2-butoxypentafluoro benzene (19 g) boiling at 64°–70° C./0.35 mmHg (73% yield based on hexafluorobenzene) was obtained by vacuum distillation.

3-Hydroxy-2-butoxypentafluorobenzene thus obtained was refluxed with dimethyl formamide (DMF) in the presence of K$_2$CO$_3$. After work up of the reaction mixture,

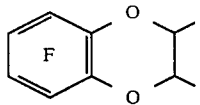

was obtained as crystal in 58% yield.
m.p. 91°–93°
$^{19}$F-NMR:
AA′BB′ type
A-163.1
B-169.5
from CFCl$_3$ reference liquid-phase photofluorination

EXAMPLE 6

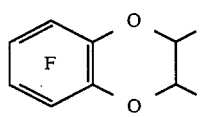

(7 g) obtained in the Example 5 was dissolved in F113 to make a 4 w/v% solution. F113 was used as the reaction medium instead of F-hexane. The photofluorination was carried out according to the method described in U.S. patent application Ser. No. 582,448, filed Feb. 22, 1984 (which is a continuation-in-part application of Ser. No. 300,273, filed Sept. 8, 1981, corresponding to EP-A-77114). After the reaction was completed, the reaction mixture was washed with saturated aqueous NaHCO$_3$, 10 w/v% aqueous sodium thiosulfate, and water in that order.

An organic layer separated was dried over Na$_2$SO$_4$.

The solvent was distilled off and that which remained was fractionally distilled using a 6-inch long vacuum-jacketed column packed with stainless steel gauze to give the fraction boiling at 126°–133° C. which is mainly the desired

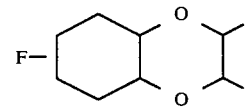

compound. The yield was 14%.

EXAMPLE 7

Cineal (8 g) was dissolved in F113 to make a 4 w/v% solution which was used as a feeding solution. FC-72 was used as a reaction medium. After fluorination was completed, the reaction mixture was treated in the same manner as the previous examples. The fraction (7.6 g) boiling at 121°–123° C. was mainly the desired F-1,3,3-trimethyl-bicyclo(2,6,2)-oxaoc. The yield was 31%.

EXAMPLE 8

A 4 w/v% solution of 2-ethyloctahydrobenzofuran (8 g) in F113 (200 ml) was pumped into the reaction medium of FC-72 (500 ml) saturated with fluorine and irradiated with a UV lamp (100 W Hg lamp). After the reaction was completed, the reaction medium was treated as in the previous examples.

The main fraction boiling at 124° C. was the desired F-2-ethyloctahydrobenzofuran (30% yield).

EXAMPLE 9

2-Methoxy-2-phenyl-F-propane was fluorinated in same manner as in the Example 8 using FC-72. The desired F-2-cyclohexyl-2-methoxypropane was obtained in 20.8% yield, along with F-isopropylhexane (9.9%) and F-isopropoxymethylcyclohexane (19.7%). The boiling range of the fraction containing F-2-cyclohexyl-2-methoxypropane and F-isopropoxymethyl-cyclohexane is 130°–132° C. F-2-cyclohexyl-2-methoxypropane

| —C(CF$_3$)$_2$ | −66.65 |
| —OCF$_3$ | −52.55 |
| —F | −179.3 |
| Fcc′ | −127.0, −115.4 |
| Fbb′ | −138.1, −121.8 |
| Faa′ | −142.1, −124.2 |

F-isopropoxymethylcyclohexane

| | |
|---|---|
| Faa' | −142.41, −124.53 |
| Fbb' | −140.30, −122.75 |
| Fcc' | −131.79, −119.76 |
| CF(ring) | −187.4 |
| CF(CF$_3$)$_2$ | −146.0 |
| CF$_2$—O | 69.16 |
| CF$_3$ | 81.28 |
| Ja-a' = 288.1 Hz | |
| Jb-b' = 286.0 | |
| Jc-c' = 297.7 | |

EXAMPLE 10

A 10 w/v% solution of 2-chlorohexafluorocyclopentenyl cyclopentyl ether (10 g) dissolved in FC-72 (100 ml) was pumped into the reaction medium of FC-72 saturated with fluorine and irradiated with an UV lamp (100 W Hg lamp). After the reaction was completed, the reaction mixture was treated as in the previous examples. The fraction boiling at 146°–149° C. was mainly the desired F-1-(2-chloropentyl)cyclopentyl ether. The yield was 29%.

EXAMPLE 11

A 20 w/v% of 2-chlorohexafluorocyclopentenyl 2,2,3,3,4,4,5,5-octafluoro-n-pentyl ether (11.6 g) dissolved in F113 was pumped into F113 saturated with fluorine and irradiated with an UV lamp (100 W Hg lamp). After the reaction was completed, the reaction mixture was treated as in the previous examples. The fraction boiling at 141°–147° C. was mainly the desired F-1-(2-chloropentyl)cyclopentyl. The yield was 38%.

EXAMPLE 12

Ten g of 2-(F-ethyl)-2-(2H-hexafluoroisopropyl)-4,5-dimethyl-1,3-dioxole was dissolved in F113 to make a 8 w/v% solution. This solution was pumped into a 1:1 by volume mixture of F113 (500 ml) and FC-72 saturated with fluorine at a temperature of −20° to −30° C. and irradiated with an UV lamp (100 W Hg lamp). After the fluorination was completed, the reaction mixture was worked up as in the previous examples.

The fractional distillation using a 6-inch vacuum jacketed column packed with a stainless steel gauze gave a fraction boiling at 130°–132° C. (5.32 g, yield 37%), which mainly consists of the desired F-2-ethyl-2-isopropyl-4,5-dimethyl-1,3-dioxole.

EXAMPLE 13

The mixture (8.6 g) of 2,4-difluoro-4-(F-ethyl)-(F-methyl)-6,7- dimethyl-1,5-dioxepan-2-ene and 4,4-difluoro-2-(F-ethyl)3-(F-methyl)-6,7-dimethyl-1,5-dioxepan -2-ene purified from the fractions obtained in the Examples 1 and 2 was fluorinated using F113 both as a solvent for the substrate and as the reaction medium. After the reaction mixture was worked up as in the previous examples, the desired F-2-ethyl-3,6,7-trimethyl-1,5-dioxepan was obtained as the fraction boiling at 134°–139° C. by the fractional distillation using a 6-inch long vacuum jacketed column. The yield was 36%.

(M-F)$^-$ (m/z 513), (M-C$_2$F$_5$)$^-$ (m/z 413) and (M-CF$_3$)$^-$ (m/z 463) were found in their negative ion mass spectra. A small amount of monochlorofluorinated derivative whose chlorine position has not yet been ascertained, concomitantly formed in this procedure, supported by the observation of (C$_{10}$F$_{19}$ClO$_2$-C$_2$F$_5$)$^-$ (m/z 431, 429) in the negative mass spectrum.

EXAMPLE 14

Decahydronaphthalene (8 g) was dissolved in F113 to make a 4 w/v% solution. This solution was pumped into a 3:1 by volume mixture of FC-73 and F113 (600 ml) saturated with undiluted fluorine at a temperature of −30° to −20° C. and irradiated with an UV lamp (100 W Hg lamp).

The reaction mixture was worked up as in the previous examples. The solvent was evaporated and that which remained was fractionally distilled using a 6-inch long vacuum jacketed column packed with stainless steel gauze. The five fractions obtained were analyzed by GC-MS and the results are summarized in the following table.

All of the compounds obtained are known and assigned by the comparison with the authentic samples.

TABLE 1

Composition of each fraction obtained by the fractional distribution of the reaction mixture of the fluorination of decahydronaphthalene

| Fraction | Boiling Range (°C.) | Amount (g) | Product Distribution | | | | | |
|---|---|---|---|---|---|---|---|---|
| | | | (I) | (II) | (III) | (IV) | (V) | (VI) |
| F-1 | 89 | 1.4 | 6.0 | 24.2 | 9.7 | 6.6 | 2.6 | 0.3 |
| F-2 | 89–136 | 3.7 | — | — | 7.0 | 7.6 | 69.0 | 11.4 |
| F-3 | 136–40 | 5.4 | — | — | 0.9 | 1.0 | 80.9 | 14.6 |
| F-4 | 140 | 2.5 | — | — | — | — | 81.2 | 17.0 |
| F-5 | 140 | 1.3 | — | — | — | — | 77.7 | 19.4 |
| Residue | | 3.4 | | | | | | |

I: F—methylcyclohexane
II: F—1,2-dimethylcyclohexane
III: F—1-ethyl-2-methylcyclohexane
IV: F—n-propylcyclohexane
V: F—trans-decalin
VI: F—cis-decalin
The products distribution of (I)–(VI) was expressed by a percentage of each peak area against the total peak area on their gas chromatogram.

No chlorine-containing compound was found in the reaction of the starting cis- and trans-decahydronaphthalene. About an 8:2 by mol mixture of trans- and cis-perfluorodecalin was obtained in 50% yield.

EXAMPLE 15

Adamantane (8 g) was dissolved in F113 to make a 4 w/v% solution. This solution was pumped into 600 ml of F113 saturated with undiluted fluorine at a temperature of −20° to −10° C. and irradiated with an UV lamp (100 W Hg lamp). The reaction mixture was worked up as in the previous examples. The solid material (sublimables at room temperature) obtained by removing the solvent was about a 1:1 by volume mixture of perfluoro and monochloropolyfluoro adamantane. Other minor components were dichloro- and trichloropolyfluoro adamantane.

The structures are supported by $M^-$ ions formed in their negative ion mass spectrum. $C_{10}F_{18}^-$ (m/z 462) $C_{10}F_{17}{}^{35}Cl^-$ (m/z 478) $C_{10}F_{16}{}^{35}Cl^{37}Cl$ (m/z 496) $C_{10}F_{15}{}^{35}Cl_2{}^{37}Cl$ (m/z 512).

While the invention has been described in detail and with reference to specific embodiments thereof, it will be apparent to one skilled in the art that various changes and modifications can be made therein without departing from the spirit and scope thereof.

We claim:

1. A liquid phase fluorination method for substituting all of the hydrogen atom(s) contained in a partially fluorinated or non-fluorinated compound by fluorine wherein
    (a) the fluorination is carried out at $-75°$ to $+100°$ C. in an inert liquid medium;
    (b) the inert liquid medium is F-hexane or 1,1,2-trichloro- 1,2,2-trifluoroethane or a mixture thereof;
    (c) undiluted $F_2$ is used;
    (d) the $F_2$ is maintained in stoichiometric excess at all times, so that the intermediate carbon radicals react with $F_2$ rather than each other;
    (e) the compound to be fluorinated, diluterd with said inert liquid medium, is metered in slowly with vigorous stirring, so that it is rapidly diluted by the solvent and its concentration is kept low compared to $F_2$, and so that efficient heat dispersal occurs and
    (f) UV illumination is used to initiate fluorination
    (g) continuing said fluorination until substantial perfluorination has been completed.

2. The liquid phase fluorination method as in claim 1, wherein the fluorination is carried out at $-30°$ to $+25°$ C.

3. The liquid phase fluorination method as in claim 1, wherein said illumination is of wavelength 240 to 330 nm.

* * * * *